United States Patent [19]

Ghent et al.

[11] Patent Number: 4,816,255
[45] Date of Patent: Mar. 28, 1989

[54] TREATMENT OF IODINE DEFICIENCY BREAST SYNDROME

[76] Inventors: William R. Ghent, 10 Montreal Street, Suite 201, Kingston, Ontario, Canada, K7L 3G6; Bernard A. Eskin, Presidential Commons, Ste. D124, Philadelphia, Pa. 19131

[21] Appl. No.: 889,947

[22] Filed: Jul. 28, 1986

Related U.S. Application Data

[63] Continuation-in-part of Ser. No. 760,950, Jul. 31, 1985, abandoned.

[51] Int. Cl.$^4$ ............................................. A61K 33/18
[52] U.S. Cl. ...................................................... 424/150
[58] Field of Search ......................................... 424/150

[56] References Cited

U.S. PATENT DOCUMENTS

| | | | |
|---|---|---|---|
| 2,816,854 | 12/1957 | Gross | 424/150 |
| 4,187,294 | 2/1980 | Ishikawa et al. | 424/150 |
| 4,259,322 | 3/1981 | Lim | 424/150 |
| 4,338,304 | 7/1982 | Kamimae et al. | 424/150 |
| 4,384,960 | 5/1983 | Polley | 210/753 |
| 4,394,376 | 7/1983 | Kamimae et al. | 424/150 |
| 4,555,347 | 11/1985 | O'Dowd et al. | 210/752 |

FOREIGN PATENT DOCUMENTS

| | | | |
|---|---|---|---|
| 35882 | 9/1981 | European Pat. Off. | 424/150 |
| 2318649 | 7/1975 | France | 424/150 |
| 406964 | 3/1934 | United Kingdom | 424/150 |
| 668968 | 3/1952 | United Kingdom | 424/150 |

OTHER PUBLICATIONS

Chem. Abst. 75:17655p (1971)—Eskin.
Chem. Abst. 84:126,316k (1976)—Stringer et al.
Chem. Abst. 90:135,752a (1979)—Eskin.
Chem. Abst. 94:41160m (1981)—Bloomer et al.
Chem. Abst. 99:136,212x (1983)—Bloomer et al.
Chem. Abst. 101:126,735r (1984)—Song et al.
Eskin B. A.—Iodine Metabolism and Breast Cancer, Transactions of the New York Academy of Science, 1970, 32(8), 911–47, See also Chem. Abstracts, at 75: 17655p (1971).
Moss et al., *Invest. Radiol.* 7, 335 (Jul.-Aug. 1972).
Zak et al., *J. Am. Pharm. Ass. Sci.* 41, 260 (1952).
Eskin et al., *Int. J. Gyn-Obs.* 8, 232 (1970).
U.S. Pharmacopea XVIII, p. 733 (1970).
Banfield et al., *J. Am. Can. Inst.* 46, 269 (1971).
Hetzel, D. S.—Iodine Deficiency Disorders (I.D.D.) and their Eradication, Lancet 12, Nov. 1983, pp. 1126–1129.
Eskin, B. A.—Iodine and Breast Cancer-A 1982 Update, Biological Trace Element Research 5, 1983, pp. 399–412.
Honour, A. J., N. B. Bryant et al—Secretion of Radio Iodine in Digestive Juices and Milk in Man, Clinical Science 11, 1952; pp. 447–462.
Beatson, G. T.—On the Treatment of Inoperable Cases of Carcinoma of the Mamma: Suggestions for a New Method of Treatment with Illustrative Cases, Lancet 2, 1896, pp. 162–165.
Kelly, F. C. and Snedden, W. W.—Prevalence and Geographical Distribution of Indemic Goitre, W.H.O. Monograph, 44; pp. 27–233.
Eskin, B. A.—Iodine Metabolism and Breast Cancer—Transactions of the New York Academy of Sciences, Series II, vol. 32, 1970; pp. 911–947.

*Primary Examiner*—Douglas W. Robinson
*Attorney, Agent, or Firm*—Robbins & Laramie

[57] ABSTRACT

This invention relates to a composition for use in the treatment of fibrocystic dysplasia which may reduce or dissipate cyst formation in the female breast and alleviate the pain and discomfort associated with this disease. More particularly, this invention relates to a composition for the treatment of fibrocystic dysplasia which is comprised of a solution of elemental iodine ($I_2$). For the purposes of this application, elemental iodine refers to diatomic iodine ($I_2$) which may also be referred to as metallic iodine or iodine metal. The elemental iodine is soluble in water, that leaves it thermodynamically free. The term "aqueous iodine" may also be used to refer to such an aqueous solution.

5 Claims, 9 Drawing Sheets

OTHER PUBLICATIONS

Vishnyakova, V. V. et al—On the Treatment of Dyshormonal Hyperplasia of Mammary Glands, Vestin. Akad. Med. Mauk. S.S.S.R. 21:19, 1966.

Roberts, M. M. et al.—Risk of Breast Cancer in Women with History of Benign Disease of the Breast—British Medical Journal, Jan. 28, 1984, vol. 288; pp. 275-278.

Peacock, Jr., Erlee—Management of Benign Disease of the Breast—American Surgeon, 1978, vol. 44(10): pp. 626-630.

Haagensen, C. D.—Disease of the Breast, Second Edition, W. B. Saunders 1971; pp. 380-383.

Gairard, B., et al—Proteins and Ionic Components in the Breast Cyst Fluid, Endocrinology of Cystic Breast Disease, Raven Press, 1983, pp. 191-195.

Gros, Ch., et al—Classification Thermographique des Cancers Mammaires—Bull Cancer (Paris) 58; pp. 351-362, 1971.

Spratt, J. S. et al—Association of Chronic Cystic Mastopathy, Xeromammographic Patterns and Cancer (prepublication).

Cole, E. N., et al—Is Prolactin a Fluid and Electrolyte Regulating Hormone in Man, J. Physiology, 1975, 252.

Cole, E. N., R. A. Gillwood et al—Serum Prolactin Concentrations in Benign Breast Disease Throughout the Menstrual Cycle, Europ. J. Cancer, vol. 13, pp. 597-603.

Minton, J. P., et al—Caffeine, Cyclic Nucleotides and Breast Disease, Surgery 1979, 86:105-109.

Fratkin, L. B.—The Hyperestrogen State, Paper presented at the North Pacific Surgery Meeting, Tacoma, Washington, 1980. (unpublished).

Moosa, A. R. et al—Thyroid Status and Breast Cancer—Royal College of Surgeons, England 53, 1973.

Greenblatt, R. B. et al—Danazol in the Treatment of Mammary Dysplasia, Fertility and Sterility 34, 1980. pp. 242-245.

Eskin, B. A. et al—Human Breast Uptake of Radioactive Iodine, Obstetrics and Gynecology vol. 44, No. 3, Sep. 1985, pp. 398-402.

Eskin, B. A.—Thyroid Hormones and Tumor Development—Chapter 6, Influences of Hormones in Tumor Development, pp. 129-156.

Riggs, D. S. et al—Investigations on the Nature of Blood Iodine.

Yunbing, G. et al—Clinical Observation of 174 Cases of Hyperplastic Cystic Disease of Breast Treated with Traditional Chinese Medicine, Journal of Traditional Chinese Medicine 3(4), 1983; pp. 291-294.

Amalric, R. et al—Dysplasies Fibro-Kystiques Aspects Thermographiques et Radiographiques, Senologia 2: 1977, 45-51.

Breast tissue from a human female with fibrocystic disease showing epithelial hyperplasia, cystic spaces and increased fibrous tissue.

FIG. I

Breast tissue from a normal female rat showing a normal configuration.

FIG. 2

Breast tissue from a female rat rendered Iodine deficient showing cystic spaces, epithelial hyperplasia and increased fibrous tissue.

FIG.3

Cystic Space     Excess Fibrous Material     Epithelial Hyperplasia

Breast tissue from a female rat on an Iodine deficient diet with oestrogens added to the model. The cystic spaces are enhanced, the epithelial hyperplasia is more marked. The increased fibrosis between the secreting acine is also present.

FIG. 4

Breast tissue from a female rat on a normal iodine containing diet with oestrogens added. The control rat shows some cyst formation and epithelial hyperplasia but without the fibrosis.

FIG.5

Breast tissue from a female rat on an iodine deficient diet with a carcinogen (Dimethyl Benzanthrene) added to the model.

FIG. 6

Some Excess Fibrous Tissue

Some Adipose Tissue Reappearing

Breast tissue from a female rat on an iodine deficient diet and then given sodium iodide as a replacement treatment. The epithelial hyperplasia has regressed, the cystic spaces have disappeared but the fibrous tissue has remained.

FIG. 7

Excess Fibrous Tissue

Breast tissue from a female rat on an iodine deficient diet then given Iodine Caseinate (Iodaminol, Desbergers Ltee, Montreal), as a replacement treatment. The epithelial hyperplasia has subsided, the cystic spaces are left but the fibrosis is unchanged.

FIG. 8

Normal Adipose Tissue

Breast tissue from a female rat on iodine deficient diet then given Elemental Iodine as replacement treatment. This has returned the microscopic picture to near normal with subsidence of the epithelial hyperplasia, the cystic spaces and the fibrosis.

FIG. 9

TREATMENT OF IODINE DEFICIENCY BREAST SYNDROME

CROSS REFERENCE TO RELATED APPLICATION

The present application is a continuation-in-part application of Ser. No. 760,950, filed July 31, 1985 now abandoned.

This invention relates to a composition for use in the treatment of fibrocystic dysplasia which reduces or dissipates cyst and fibrous tissue formation in the female breast and alleviates the pain and discomfort associated with this disease. More particularly, this invention relates to a composition for the treatment of fibrocystic dysplasia which is comprised of a solution of elemental iodine($I_2$). For the purposes of this application, elemental iodine refers to diatomic iodine ($I_2$) which may also be referred to as metallic iodine or iodine metal. The elemental iodine a solution of $I_2$ in water, and is thermodynamically free. The term "aqueous iodine" may also be used to refer to such an aqueous solution.

The nomenclature of iodine deficiency breast syndrome has a varied past with Reclus in France, Schimmelbusch in Germany and Bloodgood in the United States contributing to the confusion. Pathological nomenclature was popular for a time with the terms fibroepitheliosis, fibroadenosis and epithelial adenosis reported in the literature. Recently, the most common name applied seems to be fibrocystic disease. It is generally agreed, that all of these terms, and several more, apply to an entity characterized by painful nodular breasts and supported pathologically with cystic spaces, epithelial hyperplasia or apocrine metaplasia and interacinar fibrosis.

The etiology of the condition has remained obscure with various theories in ascendency at any one time. These have included a prolonged luteal phase, a reversal of the oestrone/oestriol ratio, increased median prolactin levels, or any upset in these complex interrelationships. All of these etiological theories are supported by good research data. More recent suggestions have implicated caffeine in coffee, tea and chocolate users and the increased oestrogen intake in milk drinkers.

It is the inventors' position that there is a common denominator in all of these concepts and this is an iodine deficient state. In this state, it is further postulated that the secreting cells of the breast are sensitized to various stimuli to produce the changes noted. This sensitization can progress to overt malignancy if a carcinogen is added to the rat model and possibly to the human female.

Clinically, the fibrocystic syndrome is the most common breast disease that affects North American women. The Cancer Committee of the American Pathologists Association (1985) estimated the incidence at 50–80% of the adult female population.

Parallel findings indicate that at least fifty percent of all North American and European women of child bearing age are suffering from fibrocystic disease (fibrocystic dysplasia). Painful breasts are common prior to the onset of menstruation and fibrocystic disease accentuates this tendency. Some women suffering from this disease have hard areas of thickening with small pellet sized masses scattered throughout the breast while other patients have marble sized cyst development. Fibrocystic disease of the breast affects one in two women between the ages of 16 and 60.

The link between iodine deficiency states and an increased incidence of breast cancer is statistically valid on a geographical basis. Demographic evidence indicates that rates of morbidity and mortality due to breast cancer are higher in areas of iodine inadequacy than in regions where iodine is readily available. Demographic surveys of Japan and Iceland show low incidences of endemic non-toxic goitre and breast cancer, while Mexico and Thailand show high incidences of goitre and breast cancer. In addition, increased breast cancer in specific endemic-goitre regions in Poland, Switzerland, Australia, and the Soviet Union have been described in various publications.

The treatment of fibrocystic disease in the past has included neglect, hormonal manipulation with birth control pills, Danazol (a masculinizing hormone), withdrawal of caffeine and cow's milk, or subcutaneous mastectomy. The treatment of this syndrome by a non-surgical technique with very low side effects would be more desirable and is offered by this invention.

Previously, iodine, a trace element in the basic physiology of humans, has received much attention in its application to thyroid function. This led, in 1929, to the addition of potassium iodine to all salt sold in Canada. The addition resulted in a marked decrease in the iodine deficiency disorders (I.D.D.) known as cretinism and endemic goitre and a drop in the incidence of hypothyroid states.

Iodides and protein bound iodines have been used to treat various other human diseases including hypercholesteremia, hyperlipemia, diabetes and tuberculosis. U.S. Pat. Nos. 4,187,294; 4,338,304 and 4,394,376, all to Kamimae et al disclose a composite containing a high amount of protein-bound iodine for the treatment of hypercholestermia, diabetes and hyperlipemia, respectively. U.S. Pat. No. 4,259,322 to Lim discloses tuberculosis medication containing sodium iodide administered by intramuscular or intravenous injections.

Recent investigations have indicated that the iodine molecule is involved in the function of various organs in the body including the salivary glands, the stomach, the liver, the ovaries and the human female breast.

Yunbing et al related hyperplastic cystic disease of the breast etiologically to dysfunction of the ovaries with elevated oestrogen level coupled with decreased progesterone level and abnormal reactivity of breast tissue to estrogen. Treatment of mammary dysplasia was directed to restoring normal ovarian function and hormonal balance of the gonad using traditional Chinese medicine. These medicines include Sargassum which contains a high iodide concentration principally in the form of potassium iodide. Among those patients treated solely with traditional medicine, Yunbing et al reported a cure rate of 65.4 percent. This is much below the rate quoted for this invention and not substantiated by animal testing.

The first mention of the thyroid/iodine associated with the human female breast was made in 1896, by Dr. Beatson, who treated metastatic breast cancer, with some success, using desiccated thyroid in large doses. Desiccated thyroid contains an abundance of protein bound iodine in addition to the active hormone thyroxine.

Carcinoma of the breast is less prevalent in patients with thyrotoxicosis than in patients with hypothyroidism, and the survival rate in the former group is enhanced as compared to hypo or euthyroid patients.

The first association of an iodine deficiency state and benign breast dysplasia was reported by Vishnyakova and Muravieva in 1966 from Russia. They reported a 78% improvement rate in women with dysplastic mastodynia treated with potassium iodide (inorganic iodine).

Studies on rats have included iodine replacement therapy in animals made iodine deficient by a Remington iodine-free diet. Employing iodide in organic salts (sodium iodide) in food at both normal and excessive levels as replacement, the breast dysplasia appeared to abate with a subsidence of epithelial hyperplasia and a loss of cystic spaces but with a continuation of the fibrosis of the syndrome.

Laboratory support for the relationship of benign fibrocystic disease and iodine deficiency was furnished by Eskin reported in 1970 in the New York Academy of Sciences Journal, which is herein incorporated by reference. Eskin was attempting to produce carcinoma in a rat model with iodine deficiency, hypothyroidism, oestrogen addition and a carcinogen. These laboratory studies were successful, but in the cellular steps to final neoplasia, microscopic changes resembling those of fibrocystic disease were produced. These changes included epithelial hyperplasia associated with mammary ducts and acinar cells, cyst formation and an increase in interacinar fibrosis. All previous animal models produced with hormonal manipulation produced hyperplasia with some cystic dilation but without the interacinar fibrosis that is characteristic of the human condition.

Therefore, by means of basic investigation in rats, a relationship was established between iodine deficiency and breast diseases particularly in the presence of sex steroids. These lesions differ histologically and metabolically from those seen in hypothyroid states.

According to Dr. Eskin's findings, breast dysplasia and neoplasia are influenced by the available iodine. Carcinogenesis occurs early in estrogen therapies in association with iodine deficiency.

The subsequent addition of iodine to iodine-deficient diets in the rat experiments reversed the breast dysplasia; once breast lesions were established, only chronic iodine replacement manages the dysplasia that is formed.

The first iodine product used in the reversal experiment was sodium iodide which resulted in reversal of the pathological changes to a degree with the subsidence of epithelial hyperplasia and cyst formation. The interacinar fibrosis remained.

Iodine caseinate, an organified form of iodine was next tested based on the proven ability of the breast tissue to deorganify iodine to secrete iodine as in organic potassium iodide in milk. The breasts' ability to organify inorganic iodine with the addition of protein molecules, some in the form of thyroxim, was proven by Eskin and reported in "Iodine in Breast Cancer-A 1982 Update" in *Biological Trace Element Research* 538.

The testing of iodine caseinate on the rat model, which first began in 1974, resulted in a reversal of the cyst formation and the epithelial hyperplasia. The interacinar fibrosis remained as a hallmark of continuing pathology.

Iodine replacement therapy investigations have been limited to animal experimentation until recently. Since the basic research had shown changes resembling fibrocystic disease in women when iodine was deficient, the clinical analogy became apparent. The clinical application of this basic research was started in 1971. Clinical treatment of women with fibrocystic disease was carried out using Lugol's iodine, which is metallic iodine in a stable alcohol based solution of potassium iodide. One undesirable characteristic of Lugol's iodine is that it has a vile taste. With the discovery of iodine caseinate as a viable replacement for Lugol's iodine, it became the basic treatment modality beginning in 1974. This protein-bound iodine, Caseoiodine-Iodaminol was administered in doses of 10 mg per day and resulted in an improvement rate of over 90%. These therapeutic trials by Ghent were enlarged in 1985 to 588 Caseoiodine patents. The patients treated with iodine caseinate experienced definite improvement both subjectively and objectively. 93.4 percent of women treated exhibited marked improvement including the disappearance of all cysts and either the complete disappearance of fibrosis in women with a short history of fibrocystic disease or with continued fibrotic changes in long-standing disease states. In addition to the very favorable results obtained through the treatment of fibrocystic disease by iodine replacement therapy, Ghent's patients did not have the massive side effects reported by Greenblatt in his treatment of mammary dysplasia with Danazol, reported in *Fertil, Steril* 34, 1980.

Most recently, beginning in August of 1984, clinical testing began by Ghent for the treatment of fibrocystic dysplasia using an oral administration of elemental iodine. As a result of treatment with aqueous iodine, 98% of patients treated have experienced dramatic reduction in breast size caused by cystic formation and fibrosis and relief of the pain both associated with this syndrome.

These clinical results parallel the laboratory results obtained in tests run concurrently by Eskin in Philadelphia. Thin section photomicrographs of breast tissue from female rats show not only the control of cysts including the abatement of epithelial hyperplasia but additionally the control and dissolution of the fibrous tissue characteristic of fibrocystic disease. Heretofore, the complete reversal of fibrocystic disease was not experienced using iodine replacement therapy. Only treatment with aqueous iodine resulted in the complete reversal of the fibrocystic dysplasia including the control of fibrosis and thus a return to normal.

It is therefore an object of the present invention to provide a method and composition for use in the treatment of fibrocystic dysplasia which results in not only the relief of pain associated with the disease, the regression of epithelial hyperplasia and the dissipation of cysts, but additionally the control and dissolution of the fibrous tissue.

In another aspect of the invention there is provided a method and composition for use in the treatment of fibrocystic dysplasia which is comprised of the use of a solution of elemental iodine.

In a further aspect of the invention there is provided a method and composition for the treatment of fibrocystic dysplasia, including the use of an aqueous solution of elemental iodine and wherein the composition is in a form for oral administration.

In an effort to overcome the disadvantages of the prior art the present invention provides a composition for the treatment of fibrocystic dysplasia, including the use of an aqueous solution of elemental iodine which may be administered orally without the vile taste of previous iodine replacement compositions, notably Lugol's iodine, and without the side effects associated with various prior art treatments.

BRIEF DESCRIPTION OF THE DRAWINGS

FIGS. 1 to 9 show phase-contrast light photo micrographs of human or rat female breast tissue showing normal cell configuration or abnormal cell development characteristic of fibrocystic disease;

FIG. 10 illustrates the solubility of iodine in water relating the concentration of iodine as a function of temperature.

FIG. 11 illustrates the results of replacement therapy with Caseoiodine.

FIG. 12 illustrates the characteristics of the study group treated with Elemental Iodine.

FIG. 13 illustrates a comparison of results of replacement therapy with Caseoiodine versus Elemental Iodine (Denovo Group).

FIG. 14 illustrates a comparison of results of replacement therapy with Caseoiodine versus Elemental Iodine (Transfer Group).

FIG. 15 illustrates the various complications manifest in the Denovo and Transfer Groups subjected to Elemental Iodine Therapy.

Figure 1:
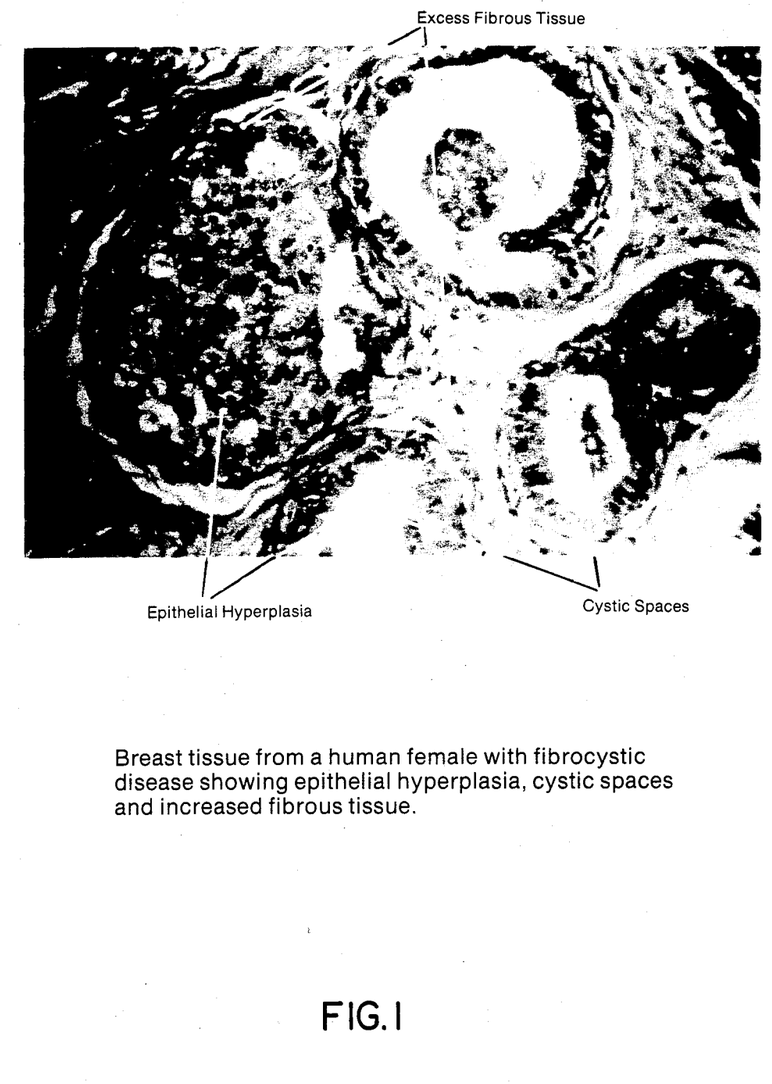
FIG. 1 shows the breast tissue from a human female with fibrocystic disease showing epithelial hyperplasia, cystic spaces and increased fibrous tissue.

Regarding FIG. 1, the photomicrograph of the breast tissue of a human female illustrates epithelial hyperlasia, cyst formation and increased fibrous tissue associated with fibrocystic disease.

Laboratory studies on rats by Eskin allow for a comparative study of the relative effect of the various prior art iodine replacement therapy including sodium iodide, iodine caseinate, and elemental iodine as a treatment for fibrocystic disease.

Figure 2:
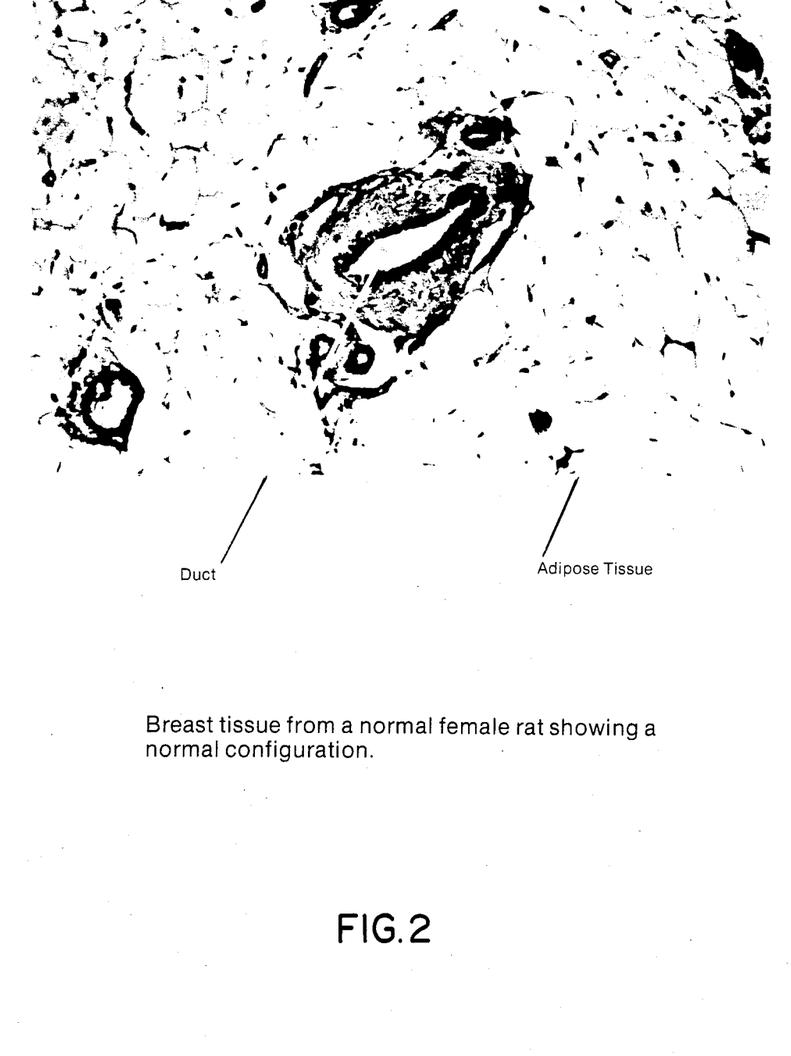
FIG. 2 shows breast tissue from a normal female rat showing normal cellular configuration.

FIG. 2 is a photo-micrograph of a normal female rat illustrating normal cellular configuration. The breast tissue includes a predominance of adipose tissue with no exhibition of epithelial hyperplasia, cyst spaces or fibrous tissue.

Figure 3:
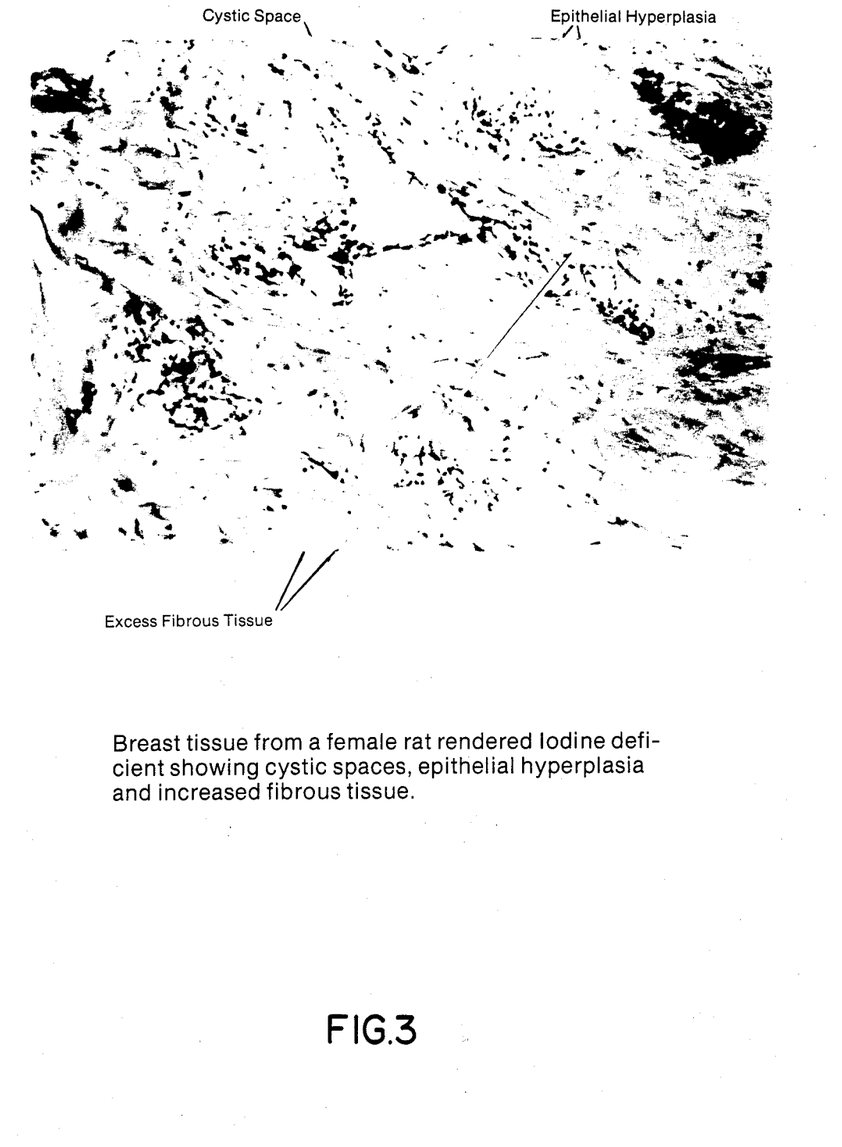
FIG. 3 shows breast tissue from a female rat rendered iodine deficient showing cystic spaces, epithelial hyperplasia associated with duct and acinar cells and increased fibrous tissues.

In comparison, FIG. 3 illustrates rat breast tissue rendered iodine deficient showing cystic spaces, epithelial hyperplasia and increased fibrous tissue characteristic of fibrocystic dysplasia. The comparison of FIGS. 2 and 3 support Eskin's previous findings relating iodine deficiency to fibrocystic disease first reported in 1970 in the New York Academy of Sciences Journal, Series 11, Volume 32, 1970; 911–947 and updated in Iodine and breast Cancer—A 1982 Update, Biological Trace Element Research, Volume 5, 1983, 399–412. The material disclosed in these articles is incorporated herein by reference.

Figure 4:
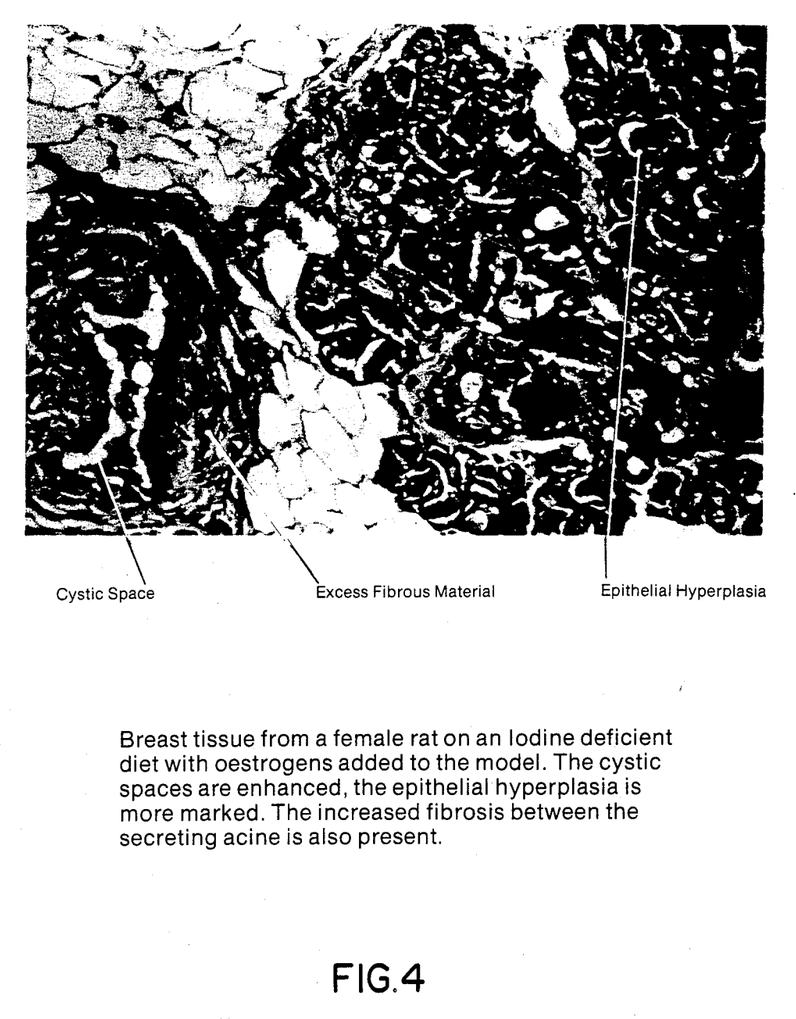
FIG. 4 shows breast tissue from a female rat on an iodine deficient diet with oestrogens added to the model.
Figure 5:
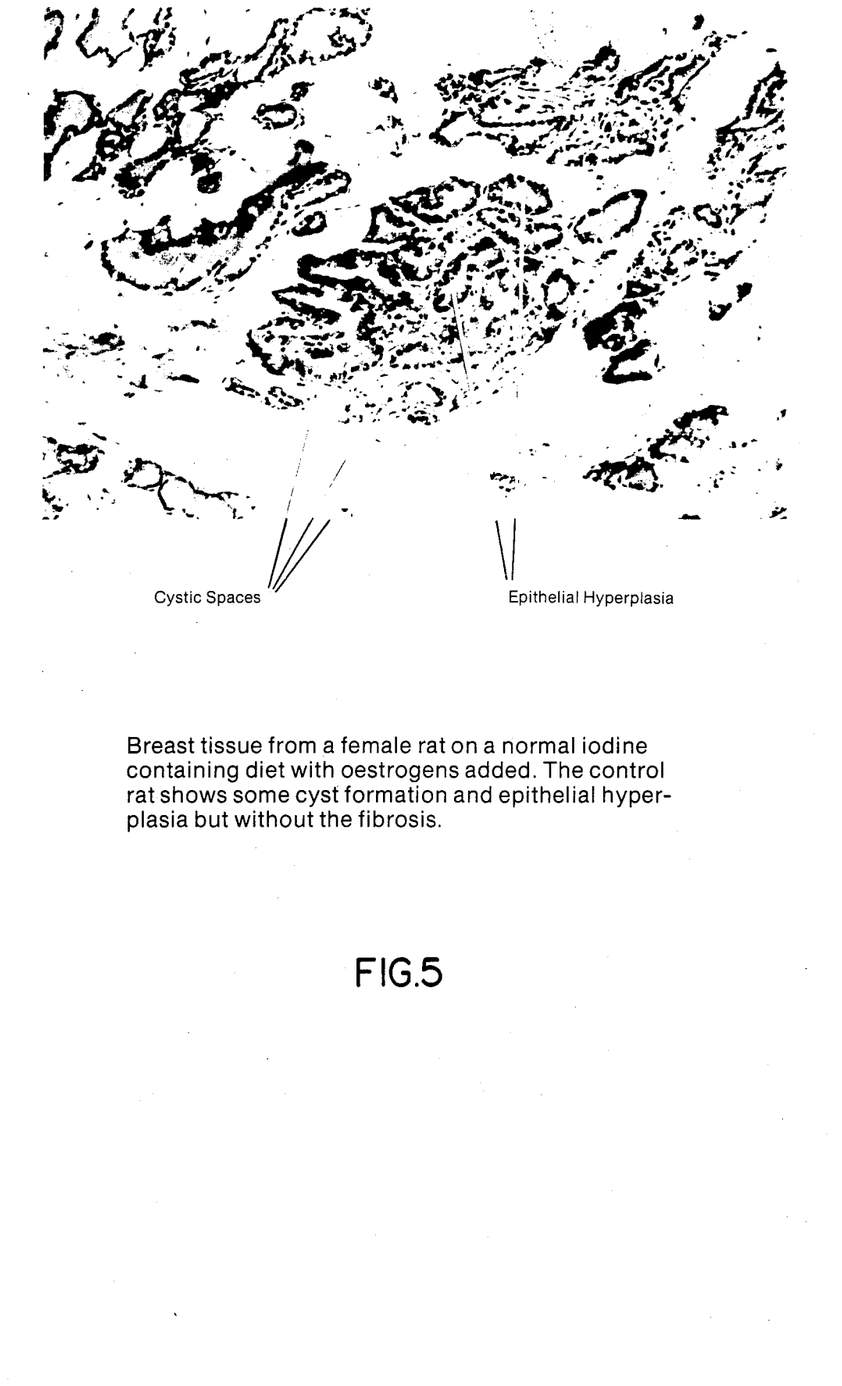
FIG. 5 shows breast tissue from a female rat on a normal iodine containing diet with oestrogens added.

FIGS. 4 and 5 show the effect of oestrogens on the breast tissue from a female rat on an iodine deficient diet.

FIG. 4 illustrates an enhancement of cystic spaces, marked increase in epithelial hyperplasia and increased fibrosis between the secreting acini. This is consistent with the findings of Fratkin reported in the paper entitled The Hyperoestrogen State presented at North Pacific Surgery Meeting in Tacoma, Wash. in 1980. A correlation was established between fibrocystic dysplasia and increased oestrogen intake in milk drinkers.

FIG. 5 is illustrative of the effect of oestrogens when added to the breast tissue from a female rat on a normal iodine containing diet. The control rat shows some cyst formation and epithelial hyperplasia but without the fibrosis.

Figure 6:
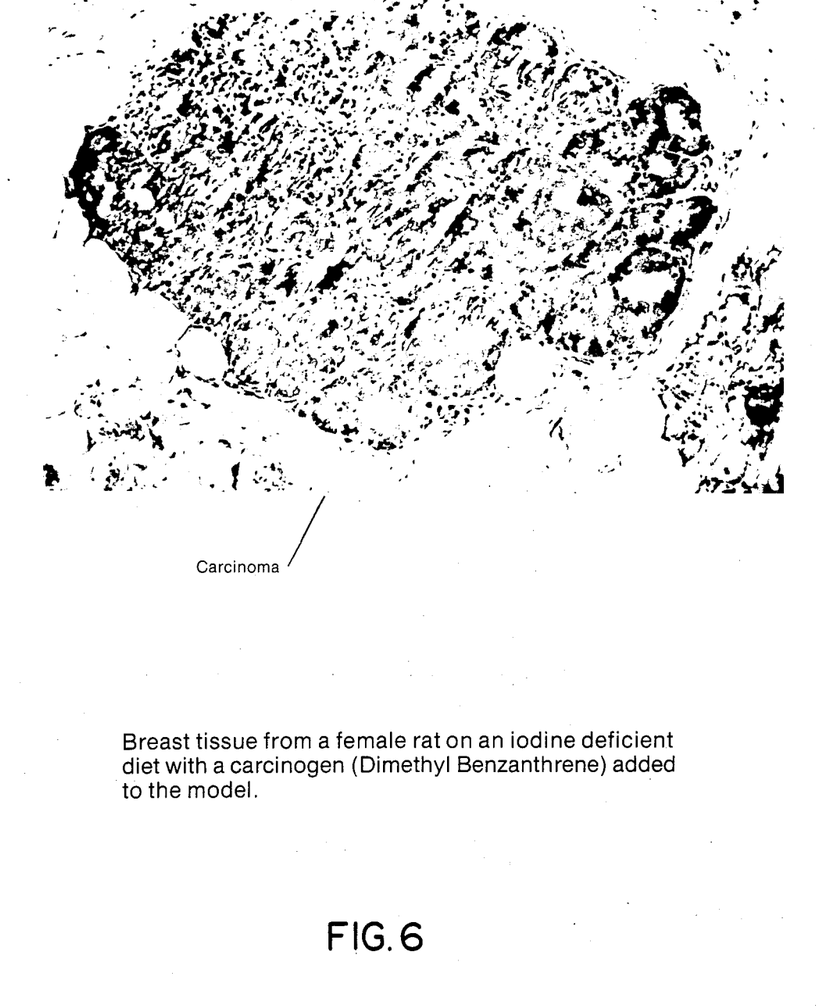
FIG. 6 shows breast tissue from a female rat on an iodine deficient diet with a carcinogen (dimethyl benzanthracene) added to the model thereby producing carcinoma.

The addition of the carcinogen, in this case dimethyl benzanthracene, to the breast tissue from a female rate on an iodine deficient diet, results in the progression from the benign state of fibrocystic dysplasia to overt malignancy as seen in FIG. 6. This finding is supportive of the inventors contention that fibrocystic disease enhances the risk of beast cancer causing sensitization of the breast tissue to various stimuli including carcinogens. This sensitization process may explain the increased incidence of breast cancer in women in areas of deficient iodine intake, reported by Moosa et al in Thyroid Status and Breast Cancer, Royal College of Surgeons, England, 53, 1973.

Figure 7:
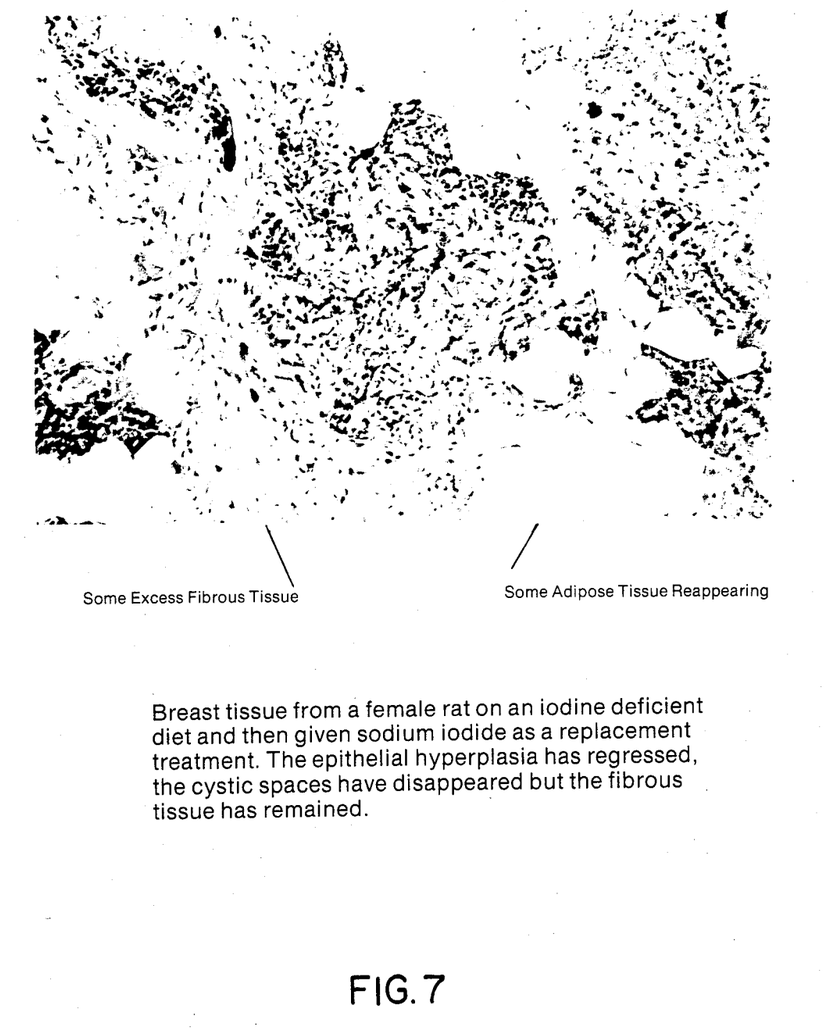
FIG. 7 shows breast issue from a female rat on an iodine deficient diet and then given sodium iodide as a replacement treatment.

FIG. 7 illustrates the effect of sodium iodine as a replacement treatment on breast tissue from a female rat on an iodine deficient diet. The epithelial hyperplasia has regressed, the cystic spaces have disappeared but the fibrous tissue remains. This is consistent with the inventors' initial research on iodine replacement therapy for fibrocystic dysplasia beginning in 1971.

Figure 8:
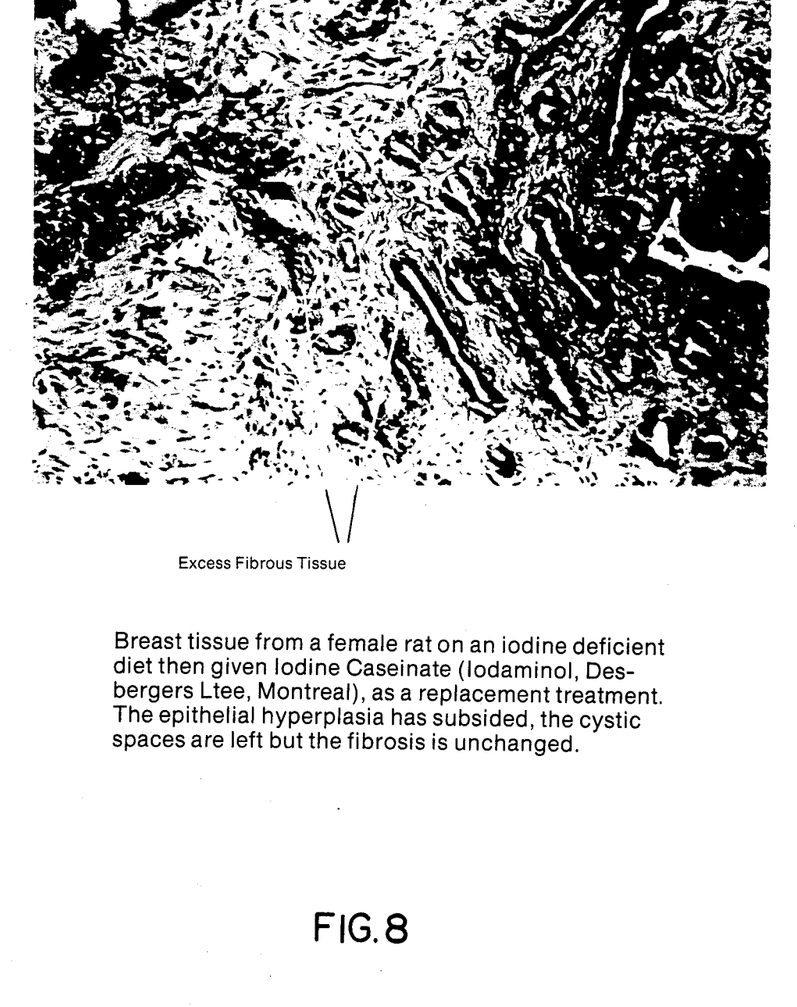
FIG. 8 shows breast tissue from a female rat on an iodine deficient diet and then given iodide caseinate (Iodaminol, Trade Mark of Desbergers Ltee, Montreal), as replacement treatment.

The effect of iodine caseinate on the morphology of rat breast tissue is illustrated in FIG. 8 which shows the subsidence of the epithelial hyperplasia, the reduction in cystic spaces, however the fibrosis remains unchanged.

Figure 9:
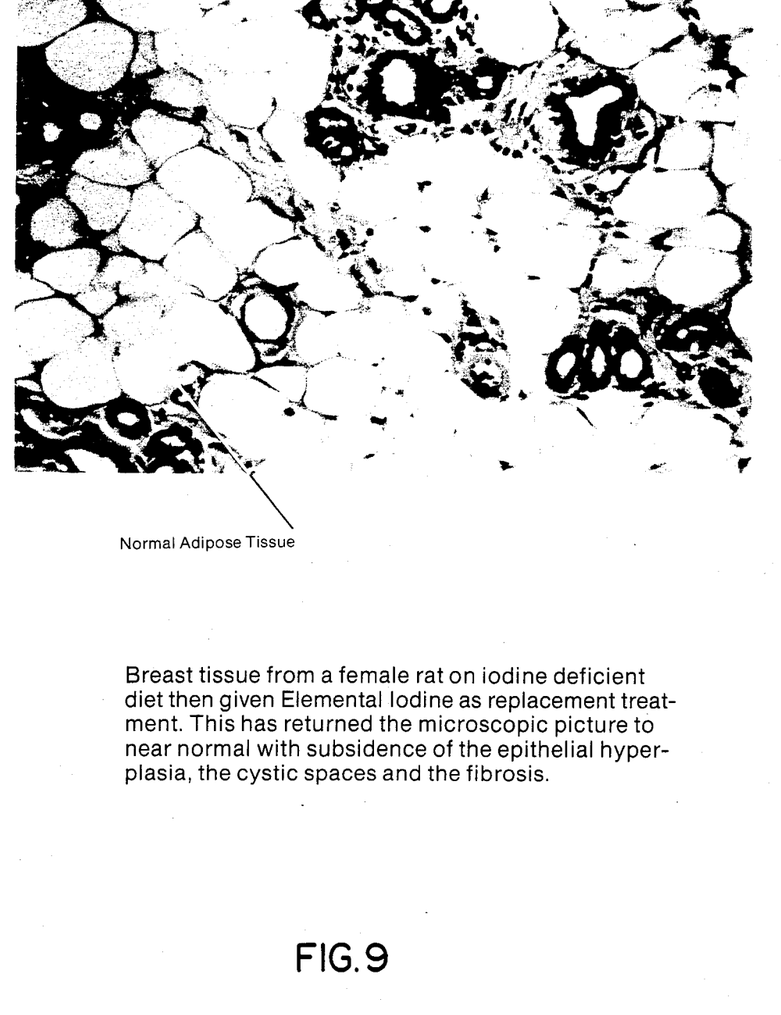
FIG. 9 shows breast tissue from a female rat on an iodine deficient diet and then given elemental iodine as replacement treatment.

In comparison, replacement treatment with elemental iodine as shown in FIG. 9 shows a reversal of tissue morphology to near normal with the return of normal adipose tissue components with subsidence of the ephithelial hyperplasia and the cyst spaces, and most notably the fibrosis (see also FIG. 2 for comparison). Heretofore, other forms of iodine replacement treatment of fibrocystic dysplasia have not been successful in the control and reversal of fibrosis. This was clearly an unexpected result.

Parallel clinical testing by Ghent supports the laboratory findings of Eskin. Iodine replacement therapy with elemental iodine began in August of 1984. At that time, 142 women with fibrocystic disease were treated with aqueous iodine. Eighty of these were patients who had been on iodine caseinate therapy for varying periods of time and have had a resolution of the cystic component but with the continued existence of fibrosis. The remainder of the sample group were patients who were started on aqueous iodine replacement therapy as the first form of treatment.

Clinical observations of the 142 cases of fibrocystic dysplasia indicated that both groups of patients had uniformly good results. The first group still had some residual discomfort and some lumpiness from the fibrosis during their treatment with iodine caseinate. However, the pain was relieved in 98% of the patients in four to six weeks after being switched to aqueous iodine treatment. In addition, the patients indicated that their breasts were softer and had reduced in size by ¼ to 1½ cups in brassiere size. This is indicative of the reversal of the fibrosis.

The second group consisting of de novo patients, had similar dramatic results in two to six weeks with control of pain, control of cysts, and control of fibrosis. These patients also noted a decrease in breast size by ¼ to 1½ cups (brassiere size). This result was obtained in 98% of patients treated.

The initial results of Elemental Iodine Therapy were encouraging with a resolution of all the elements of the triad (see FIG. 9). These results initiated further clinical testing on human volunteers suffering from fibrocystic disease. Of these, two hundred and fifty-three to date have had sufficient follow-up to allow analysis.

The subjects in this review were volunteers who had been referred with nodular, painful, swollen breasts. The diagnosis of fibrocystic disease was made on clinical examination, thermography and mammography when the age of the patient permitted such diagnosis.

As shown in FIG. 12, the study group was divided into two sections. The first group, the de novo group, numbered 108 and had not been treated previously for fibrocystic disease. The second group, the transfer group, numbered 145 and had been on iodine replacement therapy with Caseoiodine for a mean of thirty months but had experienced residual discomfort and fibrosis. The treatment of the transfer group was suspended and all patients in the series received 3-6 mg of Elemental Iodine daily.

In establishing the dosage of aqueous iodine required to effectively control all symptoms associated with fibrocystic disease, Dr. Ghent established a dosage range from between 1.2 milligrams to 6 milligrams per day of elemental iodine in aqueous solution with 3-6 milligrams per day being the most effective dose as noted above.

FIG. 10 shows the solubility of iodine in water and illustrates the relationship of iodine concentration as a function of temperature. This solubility curve was used to calculate the dosage range by Ghent and is taken from Black et al, "Use of Iodine For Disinfection" from Journal of American Waterworks Association, Volume 37, No. 11, November 1965.

Further, the half life of $I_2$ in the human appears to be eight hours and therefore a daily dose is necessary. This is supported by clinical evidence wherein 10 cases were reduced to a twice-weekly dose and within two weeks had a recurrence of symptoms. These clinical findings are supported by the inventors' previous clinical testing wherein 89.5% of patients who stopped iodine replacement therapy had a recurrence of symptoms within a nine-month period.

The patients of the study group were reassessed at four months and sixteen months. As shown in FIGS. 13 and 14 the results of the study were classified in four classes with Class 1 representing a subjective and objective return to normal. The patents of Class 2 had some residual discomfort and some residual fibrosis. Classes 3 and 4 were considered as poor results with continued pain, fibrosis and cysts.

The results in the de novo patients (FIG. 13) showed a complete subjective relief of breast pain and a clinical return to normal in 72% of patients with 26% retaining a small residual plaque of fibrosis at the four month level. As objective confirmation of the patients' changed mammary status, 76% showed a reduction in breast size that varied from ¼ to 2 cups in brassiere size.

The transfer group illustrated the most significant results with a loss of residual breast discomfort and a complete resolution of fibrosis if 74% of cases. A smaller percentage of patients (21%) were of Class 2 experiencing minor cyclical pain and some remaining soft fibrosis (see FIG. 14). It seems that the longer the duration of the fibrocystic syndrome, the longer the time required for comfort and normalcy. Reduction in breast size was as significant as the dennovo group (FIG. 13).

As noted above, Ghent and Eskin in 1985 enlarged their series of caseoiodine patents to 588 with an improvement rate of 93.4%. As shown in FIG. 11, this improvement rate was categorized originally in four classes, 1-4. The first group accounted for 43% of a subjective and objective return to normal. The second group (50.4%) had some residual premenstrual discomfort and had fibrosis that at best was only worrisome but at worst could mask early malignant changes both clinically and mammographically.

A comparison of the results obtained with caseoiodine therapy and with Elemental Iodine therapy is revealing as shown in FIG. 14. The caseoiodine therapy resulted in the return to normal without pain in 5.4% of patients (class 1), while 85.8% of patients experienced some residual premenstrual pain and fibrosis (class 2). The results after the patients were transferred to Elemental Iodine therapy are significant with 73.7% of patients returning to complete normalcy (class 1) and 21.3% again experiencing residual premenstrual pain and some fibrosis (class 2).

The various complications of Iodine replacement therapy are listed in FIG. 15. These include acne, nausea, diarrhea, hair thinning, hyper- and hypothyroid, skin rash and iodism. An increase of pain was also experienced by patients, 18.5% of the de novo group and 1.3% of the transfer group during the treatment cycle. This pain occurred three to six weeks into the treatment regime and lasted from one to three weeks. The manifestation of pain seemed to coincide with a decrease in breast size and a sudden softening of the fibrosis. Once this pain had subsided it did not recur.

Based on the two series of clinical patients and in consideration of the various complications above, elemental iodine replacement therapy has been found to be an effective treatment regime, more effective than other forms of iodine replacement therapy including treatment using caseoiodine. Iodine replacement therapy generally should be considered before mastectomy, hormonal manipulation or neglect.

We claim:

1. A method for therapeutically treating fibrocystic dysplasia of breast tissue in human patients which comprises administering to a patient an aqueous solution of elemental iodine ($I_2$) in an amount effective to cause subsidence of fibrosis in breast tissue.

2. The method of claim 1 wherein said solution is administered orally.

3. The method of claim 1 wherein the efective amount of elemental iodine is from 1.2 milligrams to 6 milligrams per day.

4. The method of claim 1 wherein the average effective amount of elemental iodine is 3 mg per day.

5. The method of claim 1 weherein the effective amount of elemental aqueous iodine is from 1.5 mg to 6 mg per day.

* * * * *